United States Patent [19]

Warrick

[11] Patent Number: 5,672,159
[45] Date of Patent: Sep. 30, 1997

[54] MEDICAL TUBING SUPPORT

[76] Inventor: Nancy J. Warrick, 300 N. 130th St., Seattle, Wash. 98133

[21] Appl. No.: 724,212

[22] Filed: Sep. 30, 1996

[51] Int. Cl.$^6$ .................................................. A61M 5/32
[52] U.S. Cl. ................... 604/179; 604/174; 128/DIG. 26
[58] Field of Search ........................... 604/174, 178, 604/179, 180; 128/DIG. 26

[56] References Cited

U.S. PATENT DOCUMENTS

| | | | |
|---|---|---|---|
| 4,018,221 | 4/1977 | Rennie | 128/185 |
| 4,313,437 | 2/1982 | Martin | 128/207.17 |
| 4,445,894 | 5/1984 | Kovacs | 604/179 |
| 4,571,245 | 2/1986 | Hubbard | 604/179 |
| 4,665,566 | 5/1987 | Garrow | 128/DIG. 26 |
| 4,707,906 | 11/1987 | Posey | 29/453 |
| 4,744,358 | 5/1988 | McGinnis | 128/207.17 |
| 4,774,946 | 10/1988 | Ackerman et al. | 128/207.18 |
| 4,821,736 | 4/1989 | Watson | 128/719 |
| 4,844,061 | 7/1989 | Carroll | 128/201 |
| 4,966,590 | 10/1990 | Kalt | 604/180 |
| 4,988,338 | 1/1991 | Taylor et al. | 604/180 |
| 5,098,399 | 3/1992 | Tollini | 604/180 |
| 5,147,322 | 9/1992 | Bowen | 604/180 |
| 5,163,914 | 11/1992 | Abel | 604/180 |
| 5,195,981 | 3/1993 | Johnson | 604/180 |
| 5,244,464 | 9/1993 | Madden et al. | 604/179 |
| 5,263,941 | 11/1993 | Cockrill | 604/179 |
| 5,368,024 | 11/1994 | Jones | 128/207.17 |
| 5,474,063 | 12/1995 | Riendeau | 128/DIG. 26 |
| 5,496,282 | 3/1996 | Militzer | 604/179 |
| 5,624,403 | 4/1997 | Jaquith | 604/179 |

*Primary Examiner*—Sam Rimell
*Assistant Examiner*—Robert V. Racunas

[57] ABSTRACT

A medical tubing support which includes a harness strap, capable of being attached around the body of the patient, a detachable pad capable of being selectively attached to the harness strap, and at least one adjustable strap pivotally attached to the detachable pad which secures ventilation circuit tubing on the detachable pad. The first end of the adjustable strap is attached to a rivet located in the center of the detachable pad. The rivet enables the adjustable strap to pivot anywhere in 360 degrees. During use, the second end of the adjustable strap is wrapped over an object to hold the object on the detachable pad. Velcro (TM) hook and loop surfaces disposed between the detachable pad and the adjustable strap enables the adjustable strap to be selectively fixed in position on the detachable pad. Velcro (TM) hook and loop surfaces provided between the detachable pad and the topside of the harness allows the detachable pad to be selectively placed on the topside of the harness. This is designed to restrict movement and allow for proper alignment of the ventilator circuit tubing if the patient is moved.

9 Claims, 6 Drawing Sheets

MEDICAL TUBING SUPPORT

BACKGROUND

1. Field of Invention

The present invention relates generally to medical tubing supports and straps, and more specifically to medical tubing supports and straps for the ventilation circuit tubing designed to be attached to endotracheal tubes and tracheostomy tubes.

2. Prior Art

Many types of straps and medical tubing supports have been designed that restrict movement of different types of medical tubing attached to various parts of a patient's body, including orifices. Adhesives and Velcro (TM) fastening are used in many of these supports.

Endotracheal tube retainers/holders have been designed to hold an endotracheal tube or tracheostomy tube securely in one position to ensure intubation of the patient, (i.e., to maintain the distal end of the tube in the patient's airway at a point just below the vocal cords, but above the bronchial tubes to ensure that both lungs can receive adequate oxygenation). Endotracheal tube and tracheostomy tube holders are usually strap or belt-like and secured by Velcro (TM). Some of these holders encircle the distal end of the endotracheal tube and are attached to another strap which encircles the back of the patient's head at the upper part of the nape of the neck, as disclosed in U.S. Pat. No. 4,844,061 to Carroll (1989). Other ideas such as U.S. Pat. No. 4,313,437 to Martin (1982), use Velcro (TM) fastening attached to a strap which is threaded through openings in flanges located on the sides of a tracheostomy tube. These inventions secure the endotracheal or tracheostomy tubes to the patient only. They do not address the security or alignment of ventilation circuit tubing which connects the endotracheal tube or tracheostomy tube to an oxygen delivery system, such as a ventilator.

Ventilatory circuit tubing consists, in part, of an inhalation and an exhalation tube which are connected to the two arms on a "Y" shaped tube made of hard plastic material. The distal end of an additional tube is connected to the main stem on the "Y". The proximal end of the additional tube is then placed on a connector piece which is attached to the endotracheal or tracheostomy tube. Perspectively looking at the patient with the ventilator circuit tubing in place, these pieces form an "upside down Y". The distal ends of the inhalation and exhalation tubes are attached to separate areas on the ventilator. Each tube is usually held and supported by a metal arm or other support device attached to the ventilator. The metal arm or support device can be adjusted in height to allow for length and extension of the tubing from the ventilator to the endotracheal tube. The manner in which endotracheal tubes and tracheostomy tubes are connected and aligned to ventilator tubing is important, because of the possibility of detachment, fluid drainage buildup in the tubing, kinking and pulling.

The ventilation circuit tubing held by a support device on the ventilator does not restrict the movement of the ventilator circuit tubing from the support device to the endotracheal tube. While tracheal tube holders or retainers are also only meant to hold the endotracheal or tracheostomy tube secure on the face or neck, some patients move around and have to be sedated or restrained while intubated because there is still danger of extubation. Therefore, if the ventilation circuit tubing is moved, the endotracheal tube can be inadvertently moved, causing extubation of the patient. There is additional danger of the ventilator circuit tubing becoming disconnected or twisted if it is not restrained. If the ventilation circuit tubing is inadvertently moved by the patient or twisted without care, fluid can also be dumped into the patient's lungs. The inhalation tubing and the exhalation tubing should be separately and securely restrained to prevent unintentional movement of either tubing. They should both be independently and easily accessible, adjustable, and maintainable in the proper angle and alignment with the endotracheal tube especially when turning the patient.

Several headbands and straps have been designed to secure the ventilation circuit tubing. The headbands are designed to prevent pressure on or obstruction of the area around the patient's face, jaws or ears from tubing or tape. However, there are many problems that can be caused by the headband design. In U.S. Pat. No. 4,744,358 to McGinnis (1988), an endotracheal tube platform is disclosed which is held in place by a harness that surrounds the head with strap attachments to hold other medical tubing and possibly ventilator circuit tubing thereto. However, the harness covers much of the face and head. Other headbands are designed only to restrain smaller medical tubing as disclosed in U.S Pat. No. 4,774,946 to Ackerman and Landis (1988). In this patent plastic yokes are disclosed that are located and fixed laterally, bilaterally on the headband to secure the tubing. The yokes can cause pressure on the head if the patient turns and lays on them. U.S. Pat. No. 4,018,221 to Rennie (1977), and U.S. Pat. No. 4,821,736 to Watson (1989), are like all headband straps in that they hold the ventilation circuit tubing upward and in front of the patient's face.

When the ventilation circuit tubing is secured on a headband, the endotracheal tube would be directed up towards the cartilaginous portion of the nose, rather than directed downward following the normal structure of the nose and nasal openings which are directed outward and downward. There may be pressure on the top part of the nose, and discomfort for the patient. If the tubing is held in this way and the patient is orally intubated, the area around the nose or eyes may be obstructed from view or may be difficult to access if a dressing is to be changed. In addition, securing the tubing by use of a headband may obstruct a view of the patient's head or face as needed in an examination or surgical procedure. The patient may have an ICP (intracranial pressure monitoring device), or a dressing on the head which requires changing, in which case the headband would have to be removed. The inhalation and exhalation tubing of the ventilation circuit would be held in an upward direction toward the top of the patient's head possibly causing fluid to dump into the patient's lungs. The lateral placement of the ventilation circuit tubing in a headband design could cause collapse of the ventilation circuitry if the patient turns to the side. Additionally, the patient may be uncomfortable having to look at the tubing in front of his face. The same problems would occur if the patient had a tracheostomy.

Some headbands and straps have secondary holding straps which are used to attach medical tubing to the headband or strap. The problem with many of the secondary holding straps is that they go over the object and fasten on the main strap in only one direction. They are not moveable to another location on the main strap for better alignment of the medical tubing. In Rennie (1977), a headband is disclosed which wraps around the patient's head and is secured by Velcro (TM) fastening. A secondary strap holds both the inhalation tubing and exhalation tubing. The strap is not adjustable in a different direction other than the direction in which it is attached. There are not separate restraining straps for each inhalation tubing and exhalation tubing, therefore each tubing can not be independently manipulated. When one tubing is intentionally unrestrained, the other one automatically becomes unrestrained. Since there is only a single strap for the inhalation tubing and the exhalation tubing, the tubings could cross over each other and cause kinking.

In other inventions, such as U.S. Pat. No. 5,244,464 to Madden, Ellers, Madden (1993), medical tubing is trapped between a main strap and a completely releasable secondary holding strap which can be disconnected allowing for multiple ways of attaching the secondary strap. The secondary holding strap is not permanently secured to the main strap. The inhalation tubing and exhalation tubing are not secured to the main strap by separate secondary straps, allowing for movement and possible detachment of either tubing when one of the tubings is manipulated. If two completely liftable separate secondary straps are used, they could accidentally overlap one another causing more tangling, since each strap would not have a fixedly common point of attachment to the main strap. It is important to have separate secondary straps for each tubing and for both straps to be connected to a common point for stability. It is equally important to allow for versatile placement of the secondary straps so the ventilation tubing can be moved to different positions.

In one embodiment of Madden, Ellers, and Madden (1993), a main strap is worn around the waist with secondary removable straps holding the ventilator tubing in place thereon. It is not practical to wear the ventilator circuit tubing strap around the waist since it may interfere with abdominal assessment, any abdominal tubings, and it would not be in close proximity to the endotracheal tube or the rest of the ventilator tubing circuitry, and possibly the ventilator. In addition the secondary straps can be accidentally moved when the patient is turned because they are not secured in any other fashion, and the patient may end up laying on the tubing.

There are several straps designed to encircle a limb, such as U.S. Pat. No. 4,571,245 to Hubbard (1986). Straps should not be used on extremities to secure the ventilation circuit tubing since extremities can move causing displacement and twisting of the tubing.

Some straps are not suitable for ventilation circuit tubing because they do not allow for easy access. The secondary holding strap for the medical tube in Hubbard (1986) is wrapped entirely around the surgical tubing, such as a catheter, and then inserted through an orifice in the middle section of itself. The end of the strap is then secured to Velcro (TM) fastening on the main strap which encircles an extremity. In U.S. Pat. No. 5,147,322 to Bowen (1992), a secondary holding strap is disclosed which uses the same principle to secure the medical tubing except an anchoring patch secured with adhesive on the patient's skin is used instead of a main strap which encircles a limb. In both designs, the tubing strap is wrapped completely around the tubing and the tubing strap would have to be unwrapped and pulled through the orifice possibly sticking to the top of the anchoring patch made of Velcro (TM) as it is pulled, and twisting the ventilation circuit tubing.

In U.S. Pat. No. 4,445,894 to Kovacs (1984), a secondary holding strap is disclosed which is sewn in the middle and attached to a main strap thereby creating two straps with opposing ends and the Velcro (TM) fastening facing upward. The medical tubing is secured by wrapping each of the opposing ends around the tubing and then fastening the end of each of the straps to the main strap. The inhalation and exhalation tubing would have two opposing end straps wrapped around each of them, thereby totaling four end straps. The straps would be difficult to access because the inhalation and exhalation tubings should be aligned in fairly close proximity and there would be several straps in a small area. One of the ventilation circuit tubings could conceivably be on top of one of the ends making it difficult to detach the strap. Two straps over one tubing takes more time to undo, and is cumbersome. If both the inhalation and exhalation tubings had to be adjusted, the health care provider would have to wrap and unwrap each strap twice. The secondary holding straps are located at a fixed point on the main strap and do not allow for a change of position of the straps if the ventilation circuit tubing has to be adjusted.

Several other ways of securing medical tubing with adhesives have been designed, such as U.S. Pat. No. 5,098,399 to Tollini (1992). A strip of adhesive securing tape is attached to the patient's skin creating a Velcro (TM) fastening tab and adhesive which holds the medical tubing in place. Part of the adhesive portion of the tape folds upon itself forming the tab. The tab folds over the medical tubing locking the tubing in place until the tab is opened again, if adjustment of the medical tubing is required. In U.S. Pat. No. 5,368,024 to Jones (1994) and U.S. Pat. No. 5,195,981 to Johnson (1993), secondary holding straps attached to a rivet is disclosed. The rivet is attached to a pad with pressure sensitive adhesive on the underside. The secondary straps secure the medical tubing. The base would have to be moved more than once if used with ventilator circuit tubing and this can not be done using adhesive.

Adhesives should not be used with ventilation circuit tubing since the tubing has to be changed and/or moved intermittently. Adhesive should not be frequently placed anywhere else on the skin once it is anchored, because it could cause irritation to the skin and may not stick a second time. Ventilation circuit tubing can not be secured with adhesive because it sticks to the tubing and could cause kinking. The position of the tubing can not be changed because adhesive is used and the strap would have to attach in only one direction. If the tape is attached to another piece of material not attached to the patient the tubing may not be in proper alignment.

Some devices designed to hold ventilator circuit tubing are not secured to the patient. In U.S. Pat. No. 5,163,914 to Abel (1992), a pillow like support pad is disclosed with a secondary strap attached using Velcro (TM) fastening material to secure a single ventilator hose from a tracheostomy. The pillow is attached to a patient's garment with safety pins on the end flanges. The bottom of the pillow is made of Velcro (TM) type fastening, which can be used in combination with the safety pins. The use of safety pins around ventilator tubing can lead to accidental puncture of the tubing. The pillow is attached to a garment on the patient such as a patient gown which may not be secure. The pillow may bounce and move if not firmly and flatly attached to something non moveable the entire length of the pillow. The secondary strap is only in one direction. There is only one secondary strap, and not two for separate attachment of the inhalation tubing and exhalation tubing.

In U.S. Pat. No. 5,263,941 to Cockrill (1993), a long flat strap is disclosed which extends over the top and across the bed and is not attached to the patient. The main strap is attached to the bed and two top secondary straps attached on either end of the main strap hold the ventilation circuit tubing in place. The secondary straps are placed only in the direction that they are sewn, not allowing for further alignment of the ventilation circuit tubing if the patient moves. The inhalation and exhalation tubings could be kinked or on top of one another under the secondary straps without being able to see that problem. The patient's head could accidentally lay on the secondary strap ends. The head would have to be lifted up in order to reposition the secondary straps and release the tubing, thereby causing movement to the endotracheal tube. Furthermore other medical equipment attached to the patient's neck or head may interfere with manipulation of the straps.

In U.S. Pat. No. 4,707,906 to Posey (1987), a medical tubing holder is disclosed that is not directly attached to the patient. However, this comprises a rigid metal strip with a rivet which has a plurality of open ended sleeve like receptacles in which surgical tubing can be placed. This strip has to be fastened on bed sheets, or patient's gown, or other instruments by a releasable spring loaded fastener, and can not be directly secured around the patient's body. This strip could be accidentally moved because it has to be attached to something other than the patient. Furthermore, a straight metal strip would not be conducive to keeping the "upside down Y" shape of the inhalation tubing and exhalation tubing in proper alignment because a single strip is used to secure both tubings, and one tubing can not be in a different angle than the other. The inhalation tubing and exhalation tubing can not be accessed independently. When the release is opened all of the other tubing attached to the metal strip is not secured. Although the strip is attached to a rivet and can be manipulated at a 360 degree angle, the rest of the metal strip is not secure to anything stationary which can cause inadvertent movement of the medical tubing.

Some other types of rivets have been designed to secure the secondary holding straps for endotracheal tubes and other types of medical tubing. These are similar to the device shown in U.S. Pat. No. 5,368,024 to Jones (1994) and U.S. Pat. No. 5,195,981 to Johnson (1993). Both devices use a rivet to secure the secondary holding straps to a pad. There are many problems using these inventions to secure ventilation circuit tubing. In U.S. Patent to Jones (1994), rivets are used to secure the secondary straps that secure an endotracheal tube, but there is no way of securing the ventilation circuit tubing to the straps, and the rivet can not be placed anywhere else once secured. U.S. Patent to Johnson (1993), requires that a secondary strap is folded upwards and away from the pad, and attaches to itself to hold medical tubing. Holding the tubing above the rivet allows the rivet to rotate the strap without the strap being secured at one place on the pad. If the ventilation tubing was secured in this way, the tubing would be allowed to rotate in a different direction than where it was originally placed, possibly causing twisting of the tubing. Both patents use adhesive to secure the pad therefore the pad is not moveable to another location if medical tubing has to be moved.

SUMMARY OF THE INVENTION

Disclosed herein is a medical tubing support which includes a body attachment means, capable of being attached around a portion of the patient, and a detachable pad capable of being selectively attached to the body attachment means. The detachable pad has at least one adjustable strap pivotally attached thereto. The adjustable strap is capable of being wrapped around an object, such as medical tubing, to hold the object on the detachable pad. The pivoting means used on the adjustable strap enables the strap to be selectively aligned on the detachable pad anywhere in 360 degrees. A fixing means is provided which enables the adjustable strap to be fixed in position on the detachable pad.

In the preferred embodiment, the body attachment means is an elliptically-shaped harness strap placed around the body of the patient. The harness strap is designed to encircle the top portion of the body diagonally, in an elliptical curve. The harness strap curves over one shoulder, extends downward over the front of the body and under the opposing arm axillary area, (the curvature of the harness strap reduces pressure on the axillary area), then extends upward diagonally across the back. The ends of the harness strap can be connected together on the lateral side of the patient, or the front side of the patient. The first end of the harness strap has a Velcro (TM) hook material strip which covers the underside thereof which attaches to the second end of the harness strap with Velcro (TM) loop material. The ends of the harness strap are then connected together to hold the harness strap in place around the patient. The ends of the harness strap are separable once connected, and can be adjusted to the size of the patient's body by moving the ends of the harness strap in opposing direction and refastening them with Velcro (TM) fastening so as to tighten or loosen the harness strap around the patient. The top side of the harness strap is made of Velcro (TM) loop material to which any Velcro (TM) hook material can be connected. The underside may be optionally made of soft, slightly stretchable, cotton material. The harness strap can be made in different lengths and sizes.

A detachable pad is selectively attached to the topside of the harness strap. In the preferred embodiment, the detachable pad is attached to the harness strap using Velcro (TM). The detachable pad has an underside made of Velcro (TM) hook material allowing placement of the detachable pad anywhere on the topside of the harness strap. The topside of the detachable pad is comprised of the softer Velcro (TM) loop material.

The detachable pad has at least one adjustable strap pivotally attached thereto by a pivoting means. In the preferred embodiment, the pivoting means is a rivet located in the center of the detachable pad. The adjustable strap is attached at its first end to the rivet by an eyelet encircling a rivet stem, thereby allowing 360 degree movement of the adjustable strap. During use, the adjustable strap wraps over the object to be held in place. In the preferred embodiment, Velcro (TM) hook material located on the underside of the second end of the strap, acts as a fixing means to selectively fix the adjustable strap in position on the detachable pad. Using two adjustable straps provides for the secured placement and independent release of the inhalation and exhalation tubings. The adjustable straps are attached directly to the detachable pad so that they are stationary until moved once rotated to a certain position. The medical tubing can be placed at any angle desired, and enables the ventilator circuit tubing to be alligned in the upside down "y" configuration.

OBJECTS AND ADVANTAGES OF INVENTION

Accordingly, as stated in the summary several objects and advantages of the proposed medical tubing support provide for a secure means for holding ventilation tubing in place close to the patient's body to prevent disconnection from the endotracheal tube and movement.

The medical tubing support is a more comfortable and stable resting place for the ventilator tubing on the patient's body rather than the head. It is not stretched above the patient's head holding the endotracheal tube up towards the cartilaginous portion of the nose as in Rennie (1977). The medical tubing is placed facing downward toward the body of the patient following the normal structure of the mouth, nose and nasal openings which are directed outward and downward. The medical tubing held in this way does not obstruct the view of the patient's head as needed in an examination, treatment or neurological exam. The medical tubing is close to the body of the patient using the harness strap, not upwards using the headband approach thereby maintaining the medical tubing in an the "upside down Y" and keeping excess fluid from becoming dumped into the endotracheal tube.

The soft cotton stretchable material on the underside of the harness strap prevents irritation on the patient's skin. Soft Velcro (TM) loop material on the topside of the harness strap allows fastening of the detachable pad's Velcro (TM) hook material anywhere on the topside of the harness strap. The underside of the first end of the harness strap which is made of Velcro (TM) hook material can be placed anywhere on the topside of the harness strap making the harness strap adjustable to any body size. The harness strap can be made in different lengths and sizes. It is disposable and washable.

Adhesive is not used on the underside of the detachable pad in the preferred embodiment of the proposed invention. Velcro (TM) hook material is used, which can allow the detachable pad to be released and fastened to the Velcro (TM) loop material located on the topside of a harness strap.

Flexibility in placement of the detachable pad maintains the proper position of the ventilator tubing when the patient is moved, or when an area of the patient's body must be accessed for treatment.

Prior art showed the holding straps placed only in one direction depending on how they were attached to the main strap, or completely releasable thereby allowing for instability and the possibility of disconnecting the tubing. A rivet securing the straps allows the straps to be placed in any direction, while allowing the straps to be secured on the pad in the position that they are placed until moved. The ventilation circuit tubing can then be placed in the proper position maintaining the patency of the tubing and comfort for the patient.

Separate holding straps for each of the inhalation and exhalation tubing also allow for independent manipulation and dumping of fluid buildup in either tubing. The straps can easily be accessed and disconnected before manipulating the tubing since they do not encompass the entire tubing, do not use tape, and are intended to go only over the top of the tubing. Various size openings can be created to accommodate different sizes in ventilator tubing since the straps can be lifted and be placed anywhere on the top of the detachable pad using of Velcro (TM).

In conclusion the medical tubing support, described herein, is a more stable place for the ventilation circuit tubing to be secured. It is adjustable, flexible and a more comfortable design for the patient than previous art which will become more apparent from the specifications and drawings.

DETAILED DESCRIPTION OF THE DRAWINGS

Figure 1:
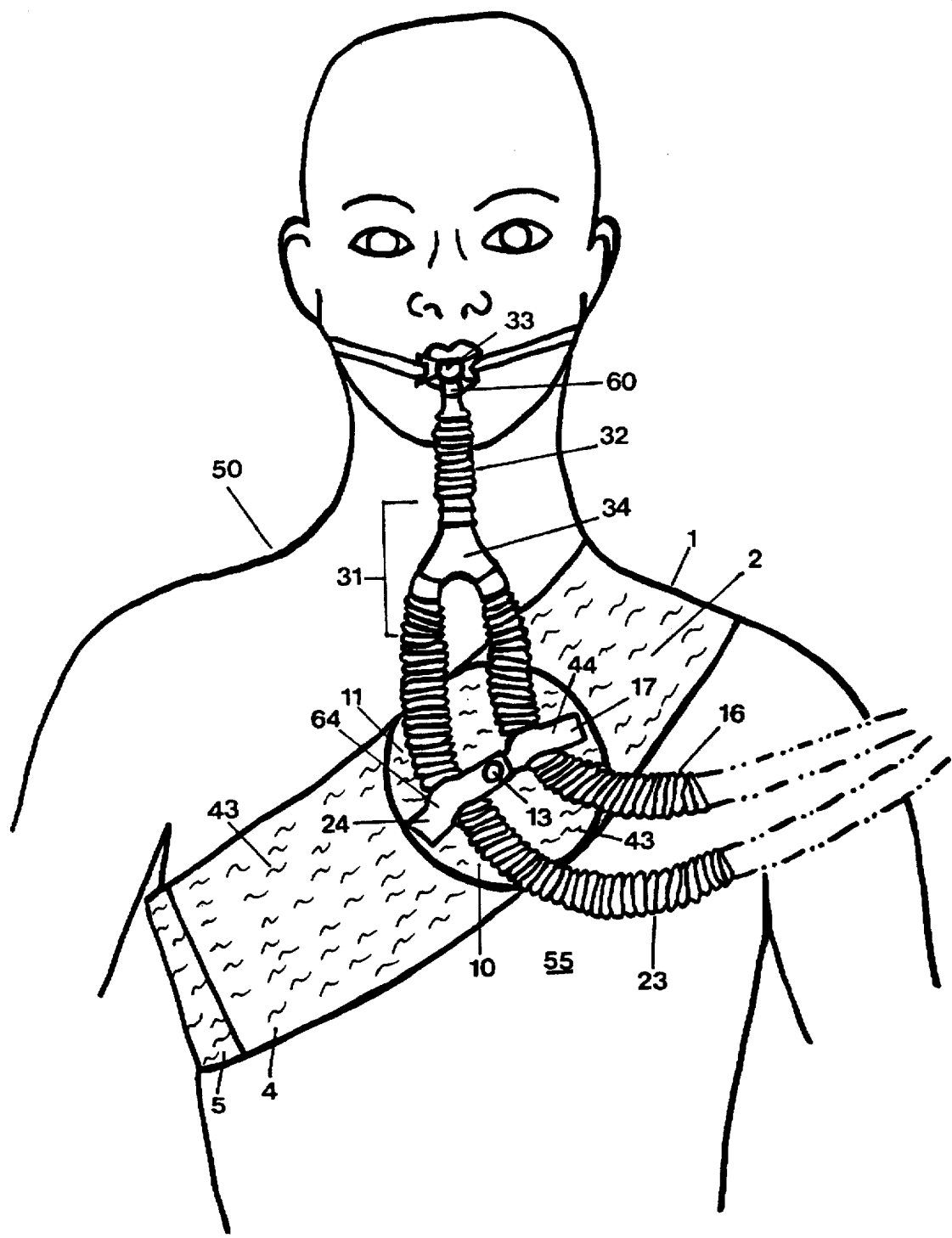
FIG. 1 illustrates the medical tubing support in use on a patient using ventilator circuit tubing.

In FIG. 1 a frontal view of an intubated patient (50) is shown with ventilation circuit tubing (31) secured and aligned in the proper upside down "y" configuration secured to harness strap (1).

The ventilation circuit tubing (31) is first discussed, moving from the top of the diagram. The endotracheal tube (33) is attached to the proximal end of endotracheal tube connector (60). The distal end of the endotracheal tube connector (60) is placed on proximal end of the additional ventilation circuit tubing (32). The distal end of the additional ventilation circuit tubing (32) is attached to the stem of the "y" shaped connector (34). The inhalation tubing (16) and exhalation tubing (23) are attached to the arms of the "y" shaped connector (34). The inhalation tubing (16) and exhalation tubing (23) continue downward and fasten to detachable pad (10) on the harness strap (1), Harness strap (1) is worn diagonally around the body of the patient (50), The harness strap first end (4) is fastened to harness strap second end (5) securing the harness strap (1) around the patient (50). The harness strap topside (2) is made of Velcro (TM) loop material (43) which allows detachable pad (10) to be place on the harness strap (1).

The detachable pad (10) is attached to the harness strap (1) and located approximately in the center area of patient's chest (55). Inhalation tubing strap (17) is secured on a rivet (13) in the center of the detachable pad (10). The inhalation tubing strap (17) is wrapped over the inhalation tubing (16) and is fastened on the detachable pad topside (11) which is composed of Velcro (TM) loop material (43). The inhalation tubing strap topside (44) is composed of soft cloth material which prevents any material from sticking to it.

Figure 2:
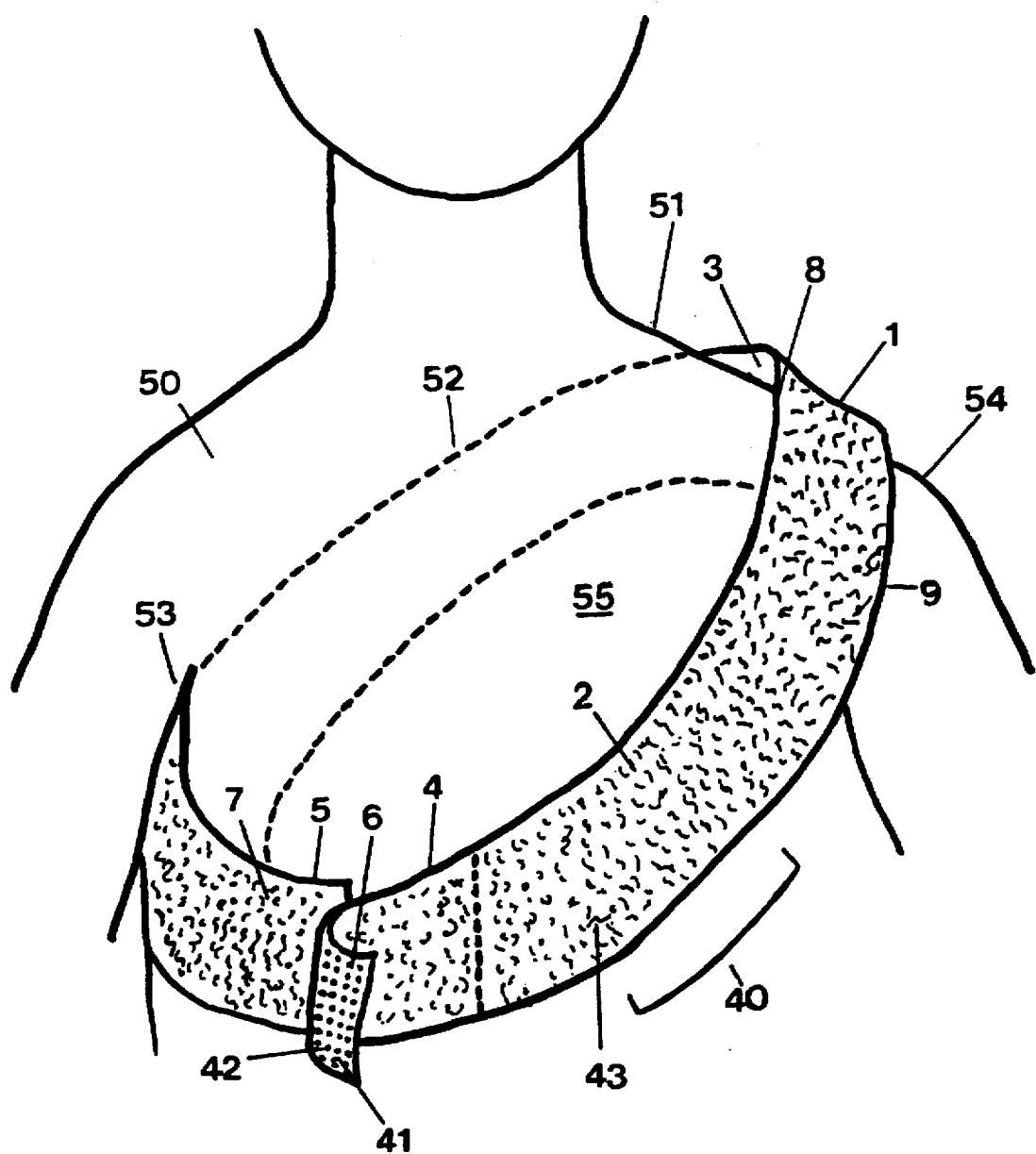
FIG. 2 is a frontal view of the harness strap positioned around the upper torso of a patient without detachable pad attached thereto.

Exhalation tubing strap (24) is secured on the rivet (13) in the center of the detachable pad (10), and is wrapped over the exhalation tubing (23). The exhalation tubing strap (24) fastens on the detachable pad topside (11). Exhalation tubing strap topside (64) is composed of soft cloth material which prevents any material from sticking to it, As shown more clearly in FIG. 2 a frontal view of the harness strap (1) is a flat piece of material approximately 3" in width (for adult size) made in elliptical curve (40) and worn diagonally on the patient (50). The harness strap (1) extends upwards and across the patient's chest (55) in a diagonal manner extending over one shoulder (54) with harness strap inner edge (8) at the nape of patient's neck (51) and harness strap outer edge (9) on the outer part of the top of the shoulder (54). The harness strap (1) extends diagonally across patient's back (52) and continues curving under and extending upwards from the opposite axilla (53) of patient (50).

There are two ends to the harness strap (1). One is harness strap first end (4) and another is harness strap second end (5). Velcro (TM) hook strip (41) approximately 4" long and 3" wide and composed of Velcro (TM) hook material (42) is sewn to harness strap first end underside (6) which is displayed partially pealed back for viewing. The harness strap first end underside (6) is partially fastened to the harness strap second end topside (7), and thereby secures the harness strap first end (4) to the harness strap second end (5), The harness strap (1) is thereby secured around the patient (50).

The harness strap topside (2) is composed of Velcro (TM) loop material (43) which encompasses the entire length of the harness strap (1). The harness strap underside (3) is composed of a soft cotton like material for comfort and encompasses the entire length of the harness strap (1).

Figure 3:
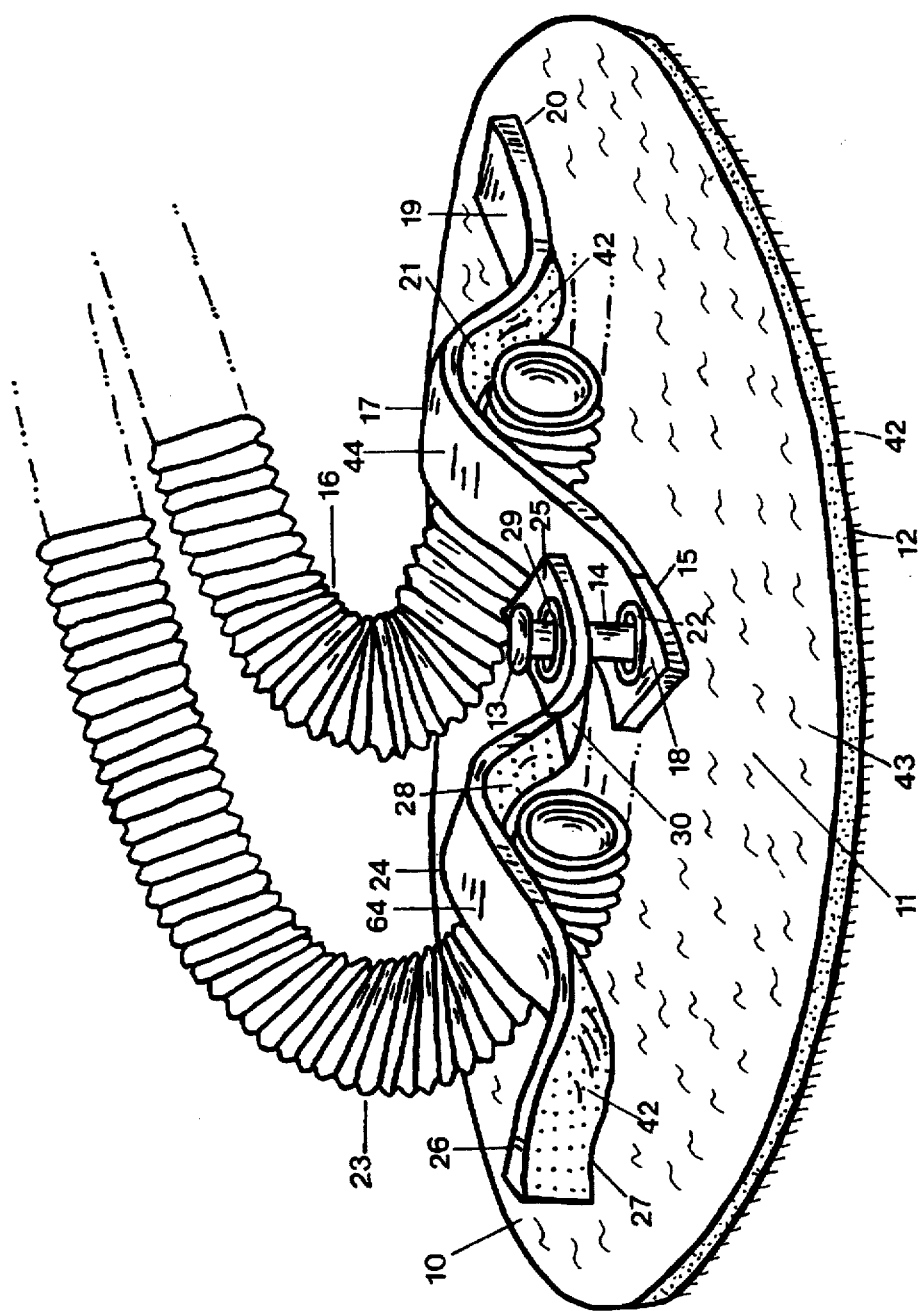
FIG. 3 is a perspective view of the detachable pad with the inhalation and exhalation tubing secured by two adjustable straps.
Figure 4:
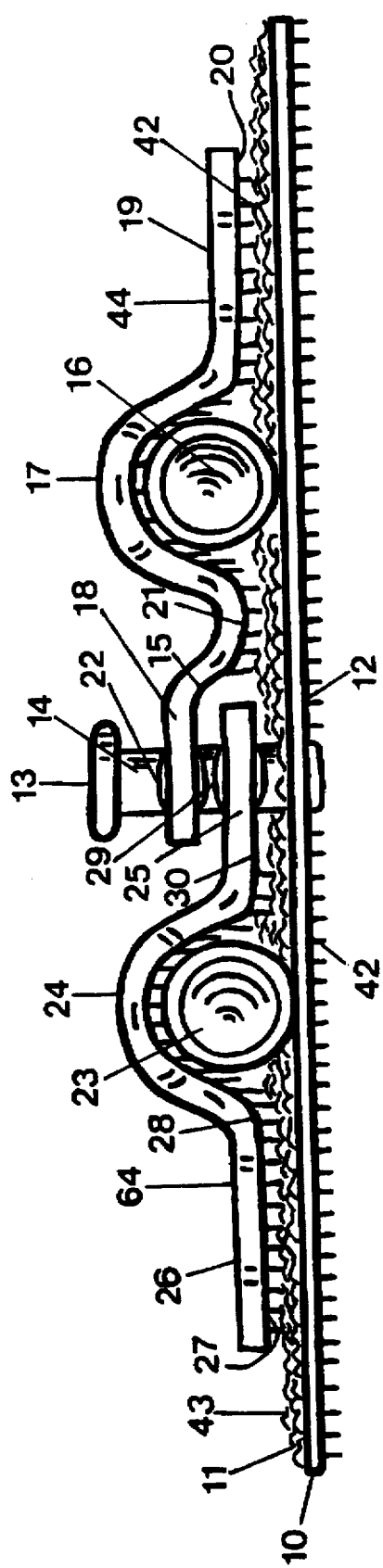
FIG. 4 is a cross-sectioned elevational side view of the detachable pad attached to the harness strap with two adjustable straps being used to secure the inhalation and exhalation tubing thereto.

The detachable pad (10) is shown more clearly in FIG. 3 and FIG. 4. The detachable pad topside is composed of Velcro (TM) loop material (43). The detachable pad underside (12) is composed of Velcro (TM) hook material (42).

The inhalation tubing strap (17) and the exhalation tubing strap (24) are secured to a rivet (13) attached to the center of detachable pad (10). The inhalation tubing strap eyelet (22) is centered on the inhalation tubing strap first end (18), and surrounds the rivet stem (14). Also surrounding the rivet stem (14) is exhalation tubing strap eyelet (29), centered on the exhalation tubing strap first end (25). In FIG. 3 the inhalation tubing strap (17) and the exhalation tubing strap (24) are lifted slightly in order to view components of both and their relationship to rivet stem (14). In FIG. 4, a cross section of the detachable pad (10), the rivet stem (14) is shown punctured through to the detachable pad underside (12).

The inhalation tubing strap (17) has two sides, the inhalation tubing strap topside (44) and the inhalation tubing strap underside (21). The inhalation tubing strap topside (44) is composed on soft cloth material and also does not allow any material to stick to it which would disturb the inhalation tubing (16). The inhalation tubing strap underside (21) has two components. The first component is the inhalation tubing strap first end underside (15). The inhalation tubing strap first end underside (15) is approximately 1" long and composed of soft cloth material that does not allow any material to stick to it thereby allowing rotation of the inhalation tubing strap (17) around the rivet stem (14). The second component is inhalation tubing strap second end underside (20), composed of Velcro (TM) hook material (42), and located on the inhalation tubing strap second end (19). The inhalation tubing strap (17) is wrapped over the inhalation tubing (16) and the inhalation tubing strap second end underside (20) is fastened to the detachable pad topside (11).

The exhalation tubing strap (24) has two sides, the exhalation tubing strap topside (64) and the exhalation tubing strap underside (28). The exhalation tubing strap topside (64) is composed on soft cloth material and also does not allow any material to stick to it which would disturb the exhalation tubing (23). The exhalation tubing strap underside (28) has two components. The first component is the exhalation tubing strap first end underside (30). The exhalation tubing strap first end underside (30) is approximately 1" long and composed of soft cloth material and does not allow any material to stick to it thereby allowing rotation of exhalation tubing strap (24) around rivet stem (14). The second component is the exhalation tubing strap second end underside (27), composed of Velcro (TM) hook material (42), and located on the exhalation tubing strap second end (26).

The exhalation tubing strap (24) is wrapped over the exhalation tubing (23) and the exhalation tubing strap second end underside (27) is fastened to the detachable pad topside (11).

Figure 5:
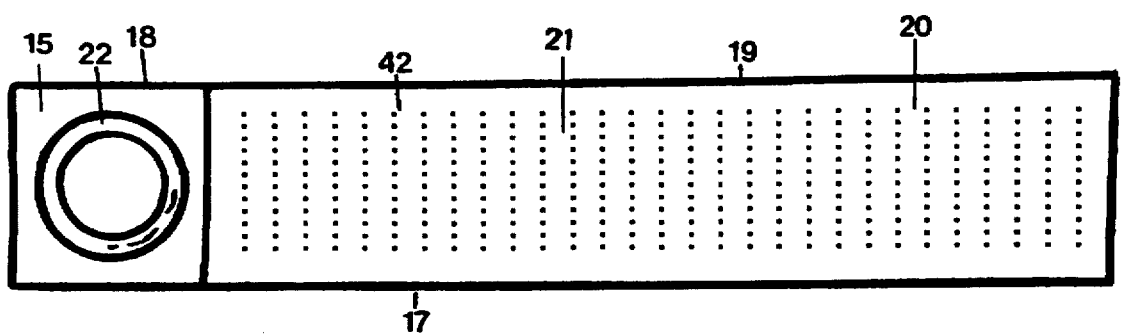
FIG. 5 is the underside plan view of the inhalation tubing strap.

In FIG. 5 the inhalation tubing strap underside (21) of the inhalation tubing strap (17) is shown straightened and flattened. The inhalation tubing strap eyelet (22) is centered on inhalation tubing strap first end (18). Soft cloth material on the inhalation tubing strap first end underside (15) continues for approximately 1". Velcro (TM) hook material (42) continues on the inhalation tubing strap second end underside (20) located on inhalation tubing strap second end (19).

Figure 6:
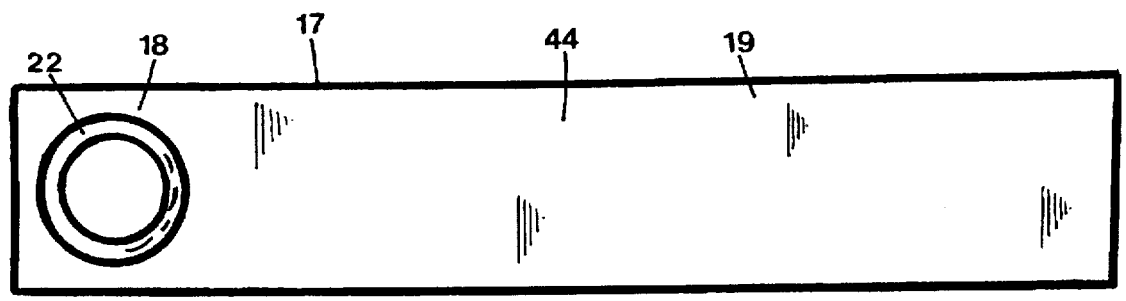
FIG. 6 is the topside plan view of the inhalation tubing strap.

In FIG. 6 the inhalation tubing strap topside (44) of the inhalation tubing strap (17) is shown straightened and flattened. The inhalation tubing strap eyelet (22) is centered on the inhalation tubing strap first end (18). The inhalation tubing strap topside (44) is made of soft cloth material and continues the entire length of the inhalation tubing strap second end (19).

Note: For FIG. 5 and FIG. 6 only the inhalation tubing strap (17) is discussed. The exhalation tubing strap (24) is the same configuration as the inhalation tubing strap (17) and was described in previous figures in order to appreciate and understand the entire design and drawings.

Operation—FIG. 1 through FIG. 4

Lay the harness strap (1) flat on the patient's chest (55). Place the harness strap first end (4) at the lower right quadrant of the patient's chest (55). Continue to place the harness strap (1) diagonally across the patient's chest (55) extending harness strap (1) upwards and over one shoulder (54) with the harness strap inner edge (8) at the nape of the patient's neck (51) and the harness strap outer edge (9) on the outer part of the top of the shoulder (54). Continue placing the harness strap (1) across the patient's back (52) diagonally, curving under and extending upwards from the opposite axilla (53) of the patient (50). Direct the harness strap second end (5), now located at the lower right quadrant of the patient's chest (55), diagonally upwards toward shoulder (54).

Move the harness strap first end (4) in an opposite direction from the harness strap second end (5). Attach the Velcro (TM) hook strip (41) on the harness strap first end underside (6) to the Velcro (TM) loop material (43) on the harness strap second end topside (7), thereby securing the harness strap (1) on the patient (50).

Place the detachable pad (10) on the harness strap topside (2) by placing the detachable pad underside (12), composed of Velcro (TM) hook material (42), on the harness strap topside (2), composed of Velcro (TM) loop material (43).

To secure the inhalation tubing (16) to the detachable pad (10), first lift up the inhalation tubing strap second end (19). The inhalation tubing strap first end (18) stays attached to the rivet stem (14). Rotate the inhalation tubing strap (17) to any position desired within 360 degrees, making sure to maintain the alignment of the ventilation circuit tubing (31) in the upside down "y" configuration. Wrap the inhalation tubing strap second end (19) over the inhalation tubing (16). Fasten the inhalation tubing strap second end underside (20), made of Velcro (TM) hook material (42), to the detachable pad topside (11).

To secure the exhalation tubing (23) to the detachable pad (10), first lift up the exhalation tubing strap second end (26). The exhalation tubing strap first end (25) stays attached to the rivet stem (14). Rotate the exhalation tubing strap (24) to any position desired within 360 degrees, making sure to maintain the alignment of the ventilation circuit tubing (31) in the upside down "y" configuration. Wrap the exhalation tubing strap second end (26) over the exhalation tubing (23). Fasten the exhalation tubing strap second end underside (27), made of Velcro (TM) hook material (42) to the detachable pad topside (11).

I claim:

1. A medical tubing support, comprising:
   a. a harness strap capable of being selectively attached around a portion of patient;

b. a detachable pad capable of being selectively attached to said harness strap;

c. at least one adjustable strap pivotally attached to said detachable pad, said adjustable strap capable of being wrapped around an object to hold said object on said detachable pad; and, d. a fixing means disposed between said detachable pad and and said adjustable strap to selectively fix said adjustable strap in position on said detachable pad.

2. A medical tubing support as recited in claim 1, wherein said harness strap has first and second ends, said first and second ends having hook and loop connector surfaces capable of being interconnected to attach said harness strap around a patient.

3. A medical tubing support, as recited in claim 1, further including said harness strap and said detachable pad having loop and hook connector surfaces, respectively, capable of being interconnected to attach said detachable pad to said harness strap.

4. A medical tubing support, as recited in claim 1, further including a pivoting means disposed between one end of said adjustable strap and said detachable pad enabling said adjustable strap to pivot 360 degrees over said detachable pad.

5. A medical tubing support, as recited in claim 1, wherein said fixing means includes loop and hook surfaces disposed between said adjustable strap and said detachable pad, respectively, capable of being interconnected to attach said adjustable strap in position on said detachable pad.

6. A medical tubing support, as recited in claim 1, further including two adjustable straps pivotally attached at one end to said detachable pad.

7. A medical tubing support, comprising:

a. a harness strap having sufficient length to be selectively attached around a portion of patient, said harness strap having first and second ends and a topside surface;

b. a detachable pad capable of being selectively attached to said topside surface of said harness strap;

c. at least one adjustable strap pivotally attached at one end to said detachable pad, said adjustable strap having sufficient length enabling said adjustable strap to be wrapped around an object to hold said object on said detachable pad; and, d. a pivoting means disposed between said adjustable strap and said detachable pad to pivotally attach said adjustable strap to said detachable pad; and, e. a fixing means disposed between said topside surface of said detachable pad and said adjustable strap to selectively fix said adjustable strap in position on said detachable pad.

8. A medical tubing support, as recited in claim 7, wherein said fixing means are a hook and loop surface disposed between said adjustable strap and said detachable pad capable of being interconnected to fix said adjustable strap on detachable pad.

9. A medical tubing support, as recited in claim 1, further including two adjustable straps pivotally attached to said detachable pad.

* * * * *